United States Patent [19]

Honda et al.

[11] Patent Number: 5,817,872
[45] Date of Patent: Oct. 6, 1998

[54] COPPER CATALYST FOR THE HYDRATION OF NITRILE AND PREPARATION THEREOF

[75] Inventors: Tadatoshi Honda; Hiroshi Ohe; Shinichiro Ichikawa; Hisaharu Kuboyama; Satoru Miyazoe, all of Kanagawa-ken, Japan

[73] Assignee: Mitsui Chemicals, Inc., Tokyo, Japan

[21] Appl. No.: 509,093

[22] Filed: Aug. 1, 1995

[30] Foreign Application Priority Data

Aug. 2, 1994 [JP] Japan ..................................... 6-181321

[51] Int. Cl.$^6$ ........................... C07C 231/06; B01J 23/00
[52] U.S. Cl. ........................ 564/127; 502/300; 502/317; 502/318
[58] Field of Search ............................ 564/127; 502/415, 502/317, 318, 300

[56] References Cited

U.S. PATENT DOCUMENTS

| | | | |
|---|---|---|---|
| 3,696,152 | 10/1972 | Habermann et al. | 564/127 |
| 4,048,114 | 9/1977 | Saunders | 502/346 |
| 4,048,226 | 9/1977 | Barber et al. | 260/561 |
| 4,086,275 | 4/1978 | Matsuda et al. | 564/127 |
| 4,234,727 | 11/1980 | Toussaint et al. | 544/178 |
| 4,302,597 | 11/1981 | Manara et al. | 564/127 |
| 4,440,956 | 4/1984 | Couvillion | 585/260 |
| 4,493,906 | 1/1985 | Couvillion | 502/346 |
| 4,867,882 | 9/1989 | O'Neill et al. | 210/684 |

FOREIGN PATENT DOCUMENTS

| | | |
|---|---|---|
| 60343/80 | 1/1981 | Australia . |
| 0009590 | 4/1980 | European Pat. Off. . |
| 0434061 | 6/1991 | European Pat. Off. . |
| 52-41241 | 10/1977 | Japan . |
| 52023002 | 9/1993 | Japan . |

OTHER PUBLICATIONS

Walter T. Reichle, *Solid States Ionics 22* "Synthesis on Anionic Clay Minerals (*Mixed Hydroxides, Hydrotalcite*)", pp. 135–141 (1986).

*Primary Examiner*—Shailendra Kumar
*Attorney, Agent, or Firm*—Burns, Doane, Swecker & Mathis, L.L.P.

[57] ABSTRACT

A copper catalyst obtained by reducing a precursor containing copper and aluminum and not containing substantially malachite and aluminum hydroxide permits preparation of amides with a high productivity and in a high selectivity by the hydration of nitrites.

24 Claims, 4 Drawing Sheets

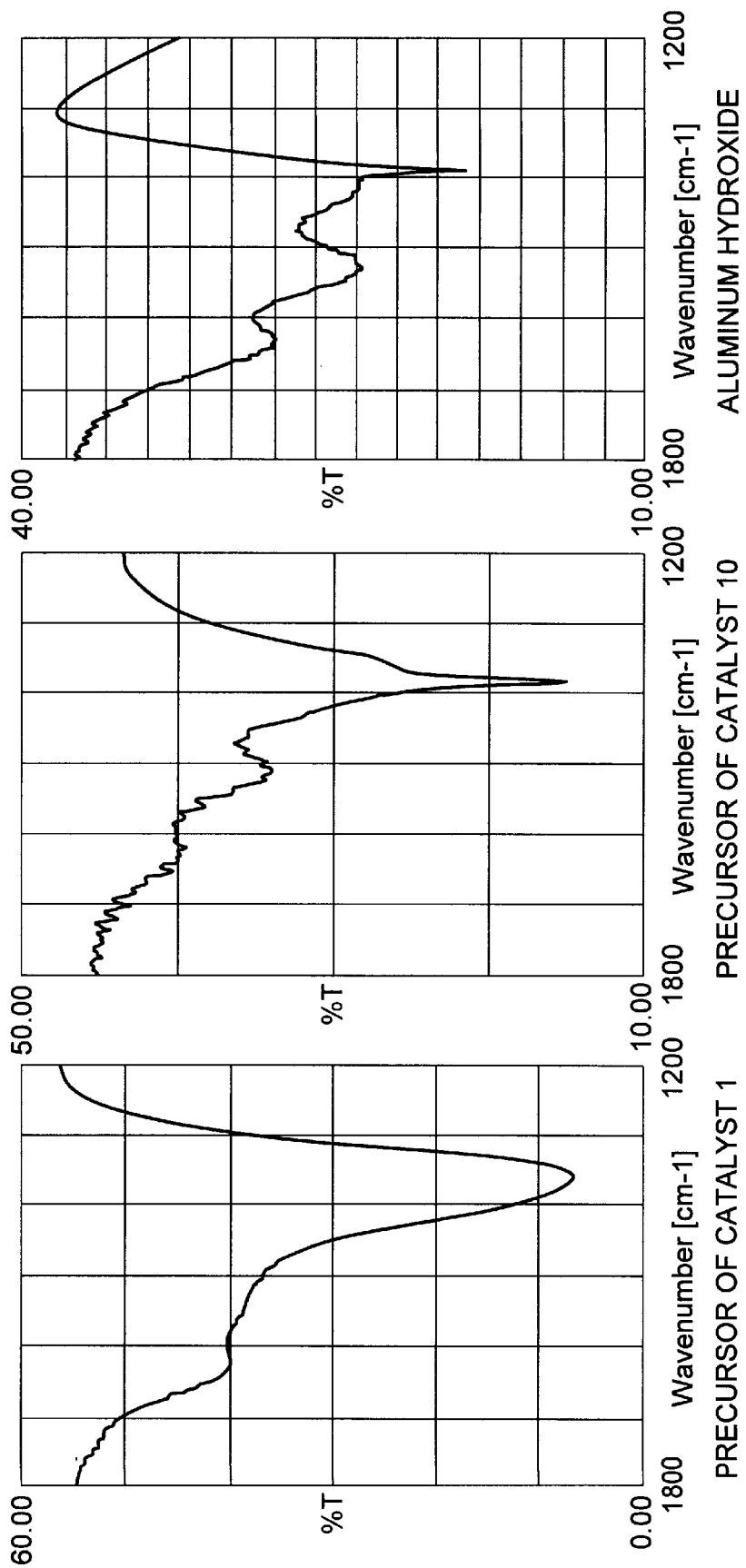

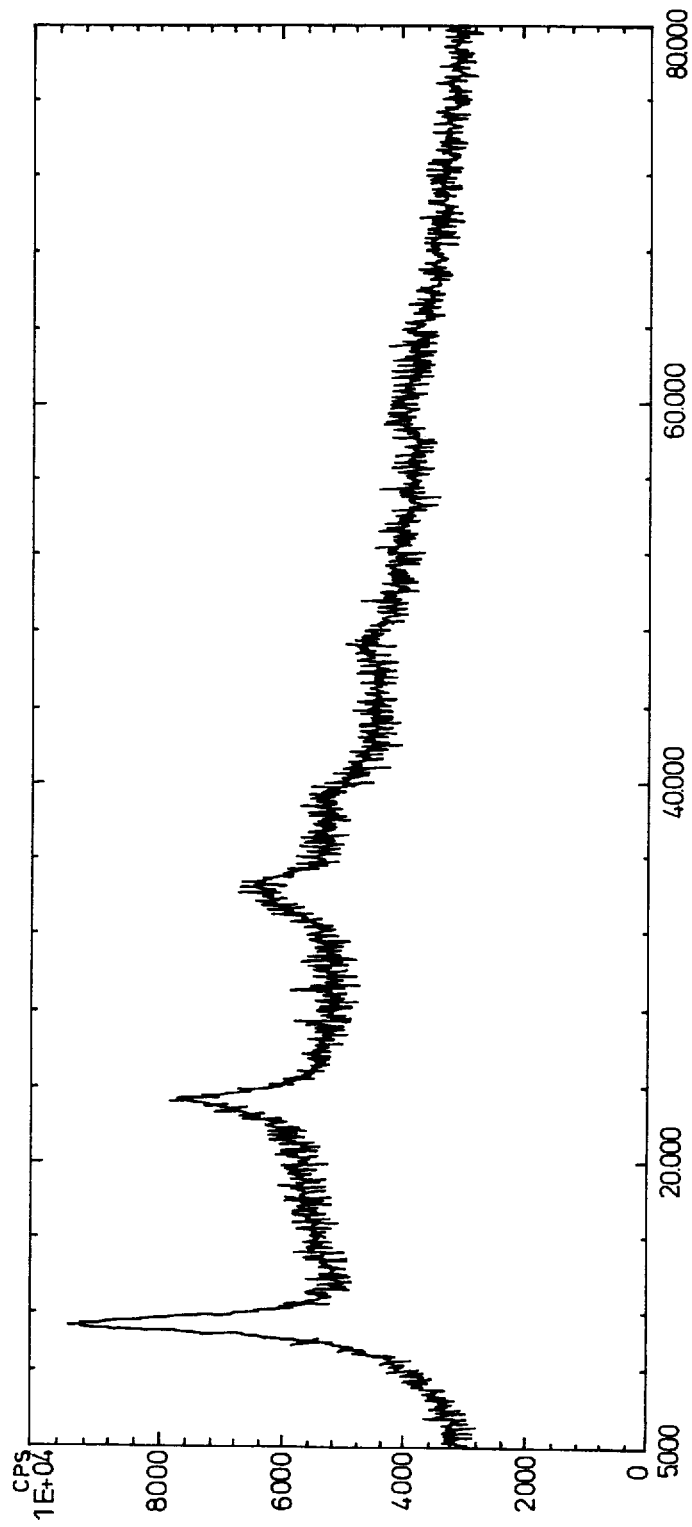

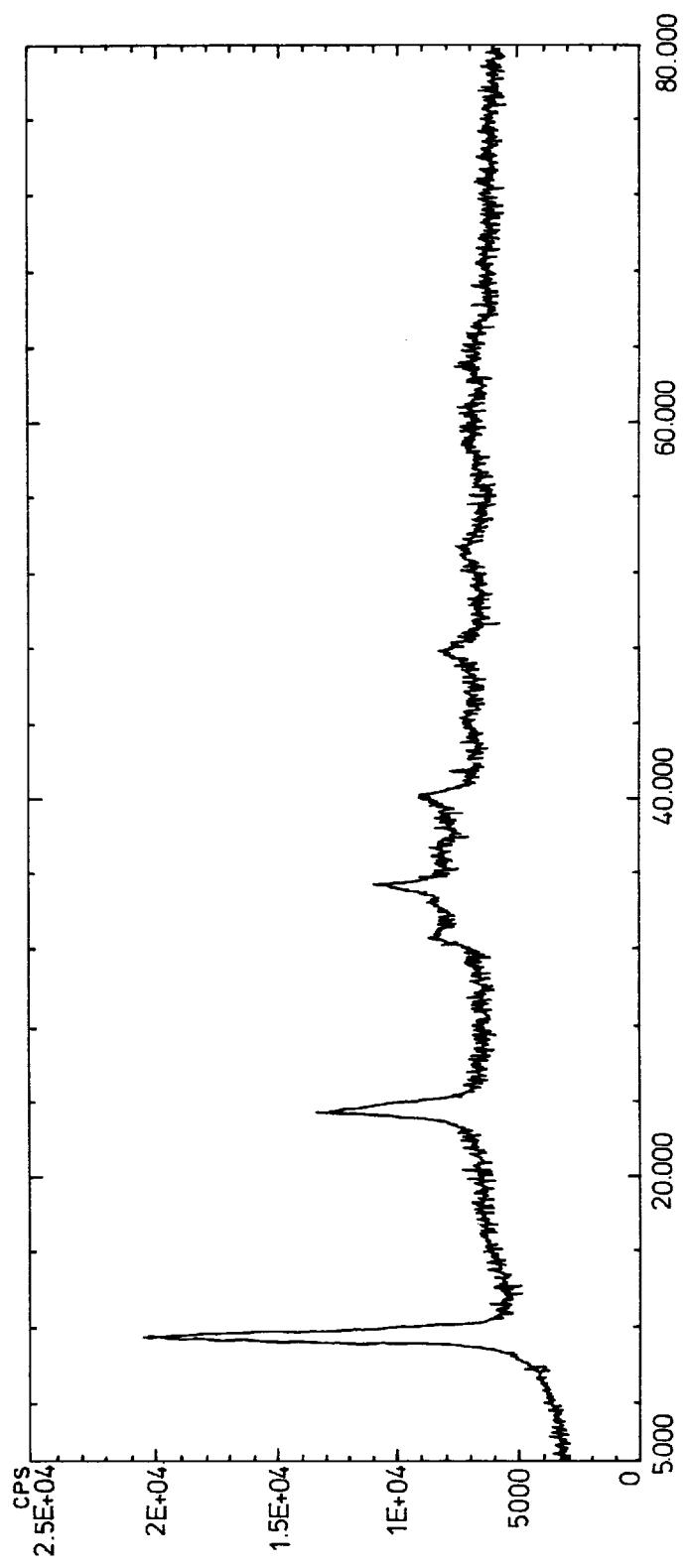

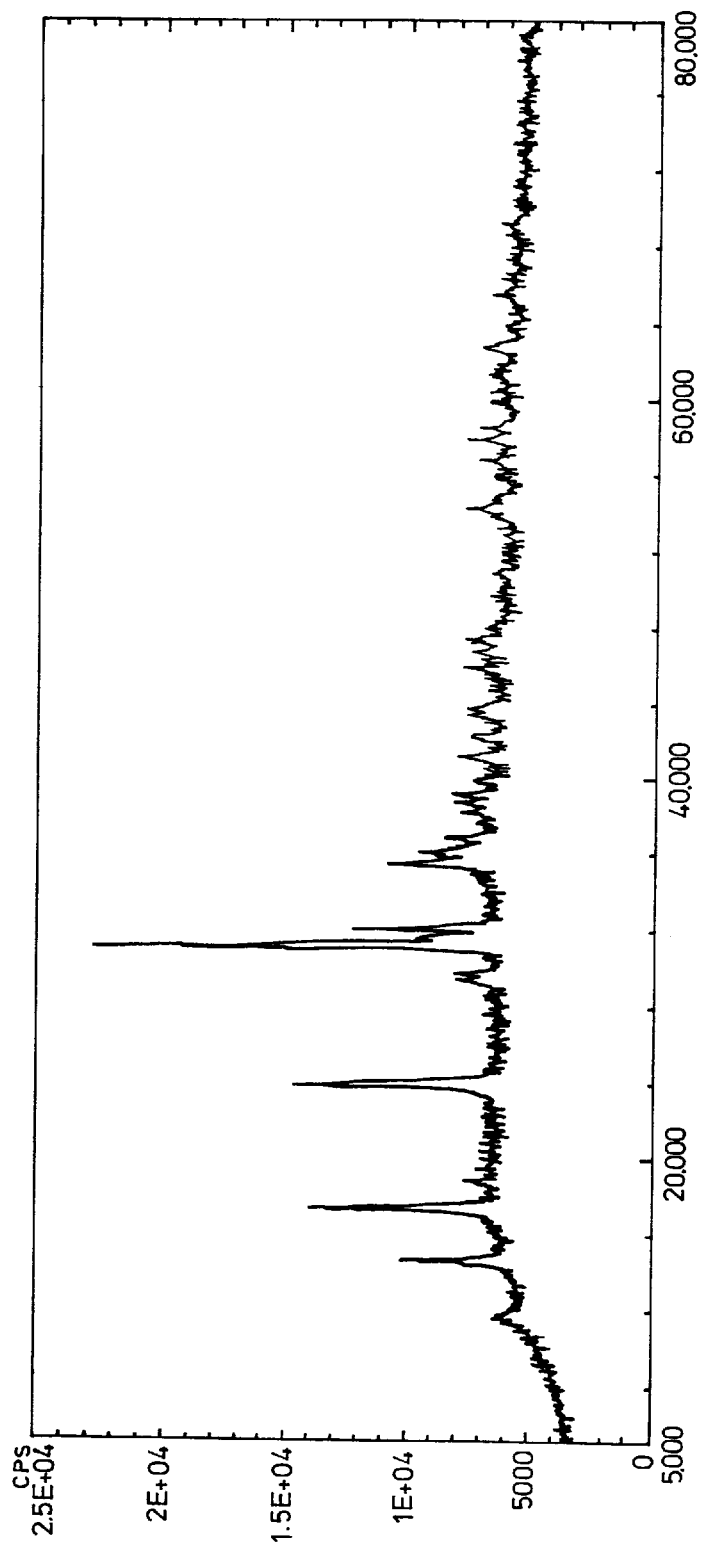

5,817,872

COPPER CATALYST FOR THE HYDRATION OF NITRILE AND PREPARATION THEREOF

BACKGROUND OF THE INVENTION

1. Field of the Invention

This invention relates to a catalyst useful for the production of an amide by the hydration of a nitrile, a method for preparing the catalyst, and a process for producing amides by reacting nitrites with water in the presence of the catalyst.

2. Description of the Related Art

It is public knowledge to produce amides by reacting nitriles with water in the presence of a catalyst. There are disclosed processes for producing acrylamide or methacrylamide by the hydration of acrylonitrile or methacrylonitrile in the presence of, for example, a copper hydride decomposition catalyst in Japanese Patent Publication No. 43924/1978, a reduced copper catalyst in Japanese Patent Publication No. 39409/1978, a partially developed Raney copper catalyst in U.S. Pat. No. 3,920,740, or a reduced copper catalyst whose precursor is a coprecipitate containing Si, W, Hg, La, Zr, Cd, Al, Pb, Mg, Fe, Mn, Co, Ni, Zn and/or Y in addition to Cu in Japanese Patent Publication No. 41241/1977. Further, Journal of Catalysis, vol. 69, p. 44 discloses a process for producing amides by the reaction of nitrites with water in the presence of a catalyst comprising copper supported on a silica-alumina carrier. In Japanese Patent Laid-Open No. 31742/1984, there is disclosed a process for producing acrylamide or methacrylamide by the hydration of acrylonitrile or methacrylonitrile, using as a catalyst a copper colloid obtained by treating a copper salt with the hydroborate of an alkali metal or an alkaline earth metal in the presence of a polymer having a protective colloid function. Although these copper catalysts shows relatively high activities, catalysts with a higher activity and higher selectivity have been desired.

OBJECT AND SUMMARY OF THE INVENTION

An object of the present invention is to provide a catalyst which is highly active and capable of synthesizing desired amides highly selectively in the reaction of nitrites with water. Another object of the present invention is to provide a process for producing desired amides by reacting nitrites with water with increased efficiency and high selectivity.

The present invention provides a method for preparing a copper catalyst for the hydration of a nitrile which comprises reducing a precursor containing copper and aluminum and not containing substantially malachite and aluminum hydroxide.

Further, the present invention provides a copper catalyst for the hydration of a nitrile which is obtained by reducing a precursor containing copper and aluminum and not containing substantially malachite and aluminum hydroxide.

Furthermore, the present invention provides a process for the hydration of a nitrile in the presence of a copper catalyst obtained by reducing a precursor containing copper and aluminum and not containing substantially malachite and aluminum hydroxide.

Use of a copper catalyst obtained by reducing a precursor containing copper and aluminum and not containing substantially malachite and aluminum hydroxide permits the synthesis of desired amides with high productivity and high selectivity in the reaction of nitrites with water.

Use of a copper catalyst obtained by reducing a hydrotalcite-like phase precursor containing copper and aluminum and not containing substantially malachite and aluminum hydroxide permits the synthesis of desired amides with high productivity and high selectivity in the reaction of nitrites with water.

BRIEF DESCRIPTION OF THE DRAWINGS

FIG. 1 provides infrared absorption spectra, in which a) is for a precursor not containing aluminum hydroxide, b) is for a precursor in which an aluminum hydroxide phase is formed, and c) is for a single aluminum hydroxide phase prepared for comparison by a precipitation method.

FIG. 2 shows an X-ray diffraction for an undeveloped hydrotalcite-like phase; FIG. 3 gives an X-ray diffraction for a hydrotalcite-like phase developed by aging; and FIG. 4 denotes an X-ray diffraction for an undeveloped hydrotalcite-like phase with malachite mixed.

DETAILED DESCRIPTION OF THE INVENTION

The precursor containing copper and aluminum and not containing substantially malachite and aluminum hydroxide can be prepared by mixing an alkali with an aqueous metal salt solution containing a copper salt and an aluminum salt.

Nitrates are generally used as the metal salt, but chlorides, sulfates, organic acid salts and the like may also be used.

The copper may be replaced by ions of a divalent metal such as Be, Mg, Ni, Co, Zn, Fe, Mn, Cd or Ca in an optional proportion. The aluminum may be replaced by ions of a trivalent metal such as Ga, Ni, Co, Fe, Mn, Cr, V, Ti, In or La in an optional proportion.

It is necessary for the aqueous metal salt solution to have an atomic ratio of trivalent metal ions to divalent metal ions in the range of from 20/80 to 45/55, preferably of from 25/75 to 30/70.

For example, Japanese Patent Publication No. 41241/1977 discloses in its specification a hydration reaction of a nitrile by the use of a catalyst obtained by reducing a precursor comprising copper and aluminum. The atomic ratio of aluminum to copper is 15/85 in the catalyst described in Example 7 of the specification, and the precursor obtained by the preparation method described therein contains malachite as illustrated in the catalyst 9 described below. Therefore, even if the hydration of a nitrile is carried out by the use of the catalyst obtained by reducing the precursor, sufficient activity and selectivity cannot be secured.

As the alkali, it is possible to use the carbonate or hydrogencarbonate of at least one alkali metal selected from the group consisting of lithium, sodium, potassium, rubidium and cesium, ammonium carbonate and ammonium hydrogencarbonate. In order to prevent the formation of an copper-ammine complex, it is preferable to use the carbonate or hydrogencarbonate of at least one alkali metal selected from the group consisting of lithium, sodium, potassium, rubidium and cesium. When sodium hydroxide or potassium hydroxide is used alone or as a mixture with the carbonate or hydrogencarbonate of the above-described alkali metal as the alkali, aluminum hydroxide is formed and therefore it is undesirable in the present invention to use sodium hydroxide or potassium hydroxide.

For instance, Solid States Ionics, vol. 22, p. 138 (1986) describes the formation of a hydrotalcite-like phase comprising copper and aluminum. However, since a mixture of sodium hydroxide and sodium carbonate is used as the alkali, the resultant precursor contains aluminum hydroxide as illustrated in the catalyst 10 described below. Therefore, even if the hydration of a nitrile is carried out by the use of a catalyst obtained by reducing the precursor, sufficient activity and selectivity cannot be secured. Further, when the reaction is carried out in a liquid flow system, a filter for separating the catalyst from the reaction fluid is disadvantageously caused to clog.

It is necessary to use the alkali in an amount of an equivalent or more, preferably of from an equivalent to two equivalents, relative to the metal salt. Use of the alkali beyond necessity is unfavored, because it reduces the rate of removing carbonates upon washing.

The alkali may be used in the state of a solid, but is preferably used in the state of an aqueous alkali solution.

To mix the aqueous metal salt solution with the aqueous alkali solution, the aqueous alkali solution may be added to the aqueous metal salt solution, or the aqueous metal salt solution may be added to the aqueous alkali solution. Alternatively, the aqueous metal salt solution and the aqueous alkali solution may be added at the same time.

No particular limitation is imposed on the slurry concentration upon forming the precipitate, and a concentration of 1 to 5% by weight is generally used. The precipitate is commonly prepared at a temperature of 30° C. or below. Preparation of the precipitate at a high temperature leads to the formation of malachite and therefore it is preferable to prepare the precipitate at a low temperature.

It is important in obtaining a coprecipitate not containing substantially malachite and/or aluminum hydroxide to remove useless carbonates as soon as possible by quickly separating the precipitate formed by mixing an aqueous metal salt solution with an aqueous alkali solution through filtration and then washing the precipitate so separated. The washing is usually carried out by repeating an operation of repulping and filtration until the pH of the washings becomes nearly neutral.

To cause a hydrotalcite-like phase to grow, useless carbonates are removed as soon as possible after preparation of the precipitate and then the precipitate is aged. The aging is effected at a temperature of from 60° C. to 200° C., preferably of from 80° C. to 120° C. It takes 10 minutes or more, preferably 30 minutes or more, to age the precipitate.

The precursor containing copper and aluminum and not containing substantially malachite and aluminum hydroxide is preferably of a hydrotalcite-like phase.

The precursor containing copper and aluminum and not containing substantially malachite and aluminum hydroxide, in which the atomic ratio of trivalent metal ions to divalent metal ions is in the range of 20/80 to 45/55, can be prepared by mixing the alkali with an aqueous solution containing copper and aluminum, in which the atomic ratio of trivalent metal ions to divalent metal ions is in the range of 20/80 to 45/55, to form a precipitate.

Further, the precursor containing copper and aluminum and not containing substantially malachite and aluminum hydroxide, in which the atomic ratio of trivalent metal ions to divalent metal ions is in the range of 25/75 to 30/70, can be prepared by mixing the alkali with an aqueous solution containing copper and aluminum, in which the atomic ratio of trivalent metal ions to divalent metal ions is in the range of 25/75 to 30/70, to form a precipitate.

In the present invention, the precursor is reduced to prepare a catalyst, and the reduction is carried out in any of a liquid or gas phase. Hydrogen is commonly used as the reducing agent, but carbon monoxide, ammonia, a lower alkane, a lower alkanol, hydrazine, a hypophosphite, sodium boron hydride and lithium aluminum hydride may also be used. The reduction temperature is generally in the range of from 100° to 500° C., preferably of from 150° to 300° C., in the gas phase. The reduction time is preferably in the range of from 1 minute to 30 hours, particularly of from 10 minutes to 15 hours. Further, in the liquid phase, the reduction is usually effected at a temperature of from 10° to 300° C., preferably of from 25° to 100° C. The reduction time in the liquid phase is generally from 30 seconds to 30 hours, preferably from 1 minute to 15 hours, depending on the kind of the reducing agent used. No particular restriction is placed on the concentration of the reducing agent. However, a low concentration is preferred so as to control sintering of the copper.

The pressure upon reducing the precursor is not particularly limited. The reduction may be effected under vacuum, at atmospheric pressure or under pressure.

The hydration reaction according to the present invention may be effected in a liquid phase as a batch reaction or a flow reaction.

Where the hydration is effected in a liquid phase as a flow reaction in the presence of a catalyst obtained by reducing a precursor which has not been aged, clogging is liable to occur at the filter part for separating the catalyst from the reaction fluid. On the contrary, with a catalyst obtained by reducing a developed hydrotalcite-like phase not containing substantially malachite and aluminum hydroxide, no clogging takes place advantageously at the filter.

No particular limitations are placed on the nitrile used in the hydration reaction according to the present invention. Illustrative examples of the nitrile include saturated aliphatic nitriles such as acetonitrile and propionitrile, unsaturated aliphatic nitriles such as acrylonitrile and methacrylonitrile, and aromatic nitriles such as benzonitrile and nicotinonitrile.

Compounds which can be produced by the present invention are amides corresponding to the nitrites, which are formed by adding water to the nitrites.

The hydration of nitrites according to the present invention may proceed at room temperature or even at a temperature below room temperature. However, the rate of reaction can be increased by raising the temperature of the reaction. A preferred temperature range is from 50° to 300° C., particularly from 50° to 150° C. The reaction time in a batch reaction is from 10 minutes to 20 hours, preferably from 30 minutes to 10 hours. The residence time in a flow reaction is from 10 minutes to 20 hours, preferably from 30 minutes to 10 hours.

No particular restriction is imposed on the amount of the water used in the hydration reaction according to the present invention. However, the water may preferably be used in an amount of several moles to several tens of moles for each mole of the nitrile.

The hydration reaction according to the present invention readily proceeds at atmospheric pressure, but it may also be carried out under pressure.

The present invention will be illustrated more specifically by the following examples.

EXAMPLES

I. Preparation of Catalyst

Catalyst 1:

First, 0.14 mole of $Cu(NO_3)_2.3H_2O$ and 0.06 mole of $Al(NO_3)_3.9H_2O$ were dissolved in water to a total volume of 300 ml. Then, 0.345 mole of sodium carbonate was dissolved in water to a total volume of 300 ml. The above-described aqueous metal salt solution and aqueous alkali solution were fed to a vessel with a stirrer in the same amounts by means of their respective quantitative pumps to prepare a precipitate. Immediately after completion of the addition, the precipitate was separated from the mother liquor by filtration. Continuously and directly, the precipitate was repulped repeatedly and washed until the washings became neutral. It took 2 hours to wash the precipitate. After the washing, the precipitate was dried at 110° C. for 5 hours. The composition of the resultant precipitate was found to be of an undeveloped hydrotalcite-like phase as a result of an X-ray diffraction measurement. An infrared spectroscopic measurement revealed that no aluminum hydroxide was present in the precipitate. The precursor thus dried was transferred to a furnace where it was heated gradually in a gas stream of 10% hydrogen and 90% nitrogen to 200° C. at which it was reduced for 5 hours to obtain a catalyst.

Catalyst 2:

A catalyst was prepared in the same manner as in the preparation of the catalyst 1 except that 0.16 mole of $Cu(NO_3)_2.3H_2O$ and 0.04 mole of $Al(NO_3)_3.9H_2O$ were used in place of 0.14 mole of $Cu(NO_3)_2.3H_2O$ and 0.06 mole of $Al(NO_3)_3.9H_2O$ and 0.33 mole of sodium carbonate was used in place of 0.345 mole of sodium carbonate. The composition of the resultant precursor was of an undeveloped hydrotalcite-like phase. An infrared spectroscopic measurement revealed that no aluminum hydroxide was present.

Catalyst 3:

A catalyst was prepared in the same manner as in the preparation of the catalyst 1 except that 0.11 mole of $Cu(NO_3)_2.3H_2O$ and 0.09 mole of $Al(NO_3)_3.9H_2O$ were used in place of 0.14 mole of $Cu(NO_3)_2.3H_2O$ and 0.06 mole of $Al(NO_3)_3.9H_2O$ and 0.37 mole of sodium carbonate was used in place of 0.345 mole of sodium carbonate. The composition of the resultant precursor was of an undeveloped hydrotalcite-like phase. An infrared spectroscopic measurement revealed that no aluminum hydroxide was present.

Catalyst 4:

A catalyst was prepared in the same manner as in the preparation of the catalyst 1 except that potassium carbonate was used in place of sodium carbonate. The composition of the precursor after the drying was of an undeveloped hydrotalcite-like phase. An infrared spectroscopic measurement revealed that no aluminum hydroxide was present.

Catalyst 5:

A catalyst was prepared in the same manner as in the preparation of the catalyst 1 except that the slurry obtained after the washing was aged at 100° C. for 2 hours. The composition of the precursor after the aging was found to be of a developed hydrotalcite-like phase as a result of an X-ray diffraction measurement. An infrared spectroscopic measurement revealed that no aluminum hydroxide was present.

Catalyst 6:

A catalyst was prepared in the same manner as in the preparation of the catalyst 5 except that 0.12 mole of $Cu(NO_3)_2.3H_2O$ and 0.04 mole of $Al(NO_3)_3.9H_2O$ were used in place of 0.14 mole of $Cu(NO_3)_2.3H_2O$ and 0.06 mole of $Al(NO_3)_3.9H_2O$ and 0.27 mole of sodium carbonate was used in place of 0.345 mole of sodium carbonate. The composition of the precursor after the aging was found to be of a developed hydrotalcite-like phase as a result of an X-ray diffraction measurement. An infrared spectroscopic measurement revealed that no aluminum hydroxide was present.

Catalyst 7:

A catalyst was prepared in the same manner as in the preparation of the catalyst 1 except that a mixture of 0.12 mole of $Cu(NO_3)_2.3H_2O$ and 0.02 mole of $Zn(NO_3)_2.6H_2O$ was used in place of 0.14 mole of $Cu(NO_3)_2.3H_2O$. The composition of the precursor after the drying was found to be of an undeveloped hydrotalcite-like phase as a result of an X-ray diffraction measurement. An infrared spectroscopic measurement revealed that no aluminum hydroxide was present.

Catalyst 8:

A catalyst was prepared in the same manner as in the preparation of the catalyst 1 except that ammonium carbonate was used in place of sodium carbonate. The composition of the precursor after the drying was of an undeveloped hydrotalcite-like phase. An infrared spectroscopic measurement revealed that no aluminum hydroxide was present.

Catalyst 9:

First, 0.17 mole of $Cu(NO_3)_2.3H_2O$ and 0.03 mole of $Al(NO_3)_3.9H_2O$ were dissolved in 400 ml of water. Then, 0.215 mole of ammonium carbonate was dissolved in 400 ml of water. The aqueous metal salt solution and the aqueous alkali solution were added simultaneously to a vessel with a stirrer. After completion of the addition, the mixture was stirred continuously for about 30 minutes. The precipitate so obtained was separated by filtration and repulped repeatedly until the washings became neutral. It took 2 hours to wash the precipitate. After the washing, the precipitate was dried at 110° C. for 5 hours. The composition of the coprecipitate after the drying was found to be of an undeveloped hydrotalcite-like phase and malachite as a result of an X-ray diffraction measurement. An infrared spectroscopic measurement indicated that no aluminum hydroxide was present. The coprecipitate having undergone the drying was baked at 280° C., allowed to cool, and then heated gradually in a stream of 20% hydrogen and 80% nitrogen to 175° C. at which it was reduced for 4 hours to obtain a catalyst.

Catalyst 10:

A catalyst was prepared in the same manner as in the preparation of the catalyst 1 except that a mixture of 0.03 mole of sodium carbonate and 0.4 mole of sodium hydroxide was used in place of 0.345 mole of sodium carbonate. The composition of the precursor after the drying was of a hydrotalcite-like phase as a result of an X-ray diffraction measurement. An infrared spectroscopic measurement indicated the presence of an aluminum hydroxide phase.

Catalyst 11:

A catalyst was prepared in the same manner as in the preparation of the catalyst 1 except that 0.10 mole of $Cu(NO_3)_2.3H_2O$ and 0.10 mole of $Al(NO_3)_3.9H_2O$ were used in place of 0.14 mole of $Cu(NO_3)_2.3H_2O$ and 0.06 mole of $Al(NO_3)_3.9H_2O$ and 0.37 mole of sodium carbonate was used in place of 0.345 mole of sodium carbonate. The composition of the resultant precursor was of an undeveloped hydrotalcite-like phase. An infrared spectroscopic measurement indicated the presence of aluminum hydroxide.

Catalyst 12:

A catalyst was prepared in the same manner as in the preparation of the catalyst 1 except that 0.18 mole of $Cu(NO_3)_2.3H_2O$ and 0.02 mole of $Al(NO_3)_3.9H_2O$ were used in place of 0.14 mole of $Cu(NO_3)_2.3H_2O$ and 0.06 mole of $Al(NO_3)_3.9H_2O$ and 0.315 mole of sodium carbonate was used in place of 0.345 mole of sodium carbonate. The composition of the resultant precursor was of an undeveloped hydrotalcite-like phase and malachite. An infrared spectroscopic measurement revealed that no aluminum hydroxide was present.

Catalyst 13:

A catalyst was prepared in the same manner as in the preparation of the catalyst 1 except that 0.06 mole of $Cu(NO_3)_2 \cdot 3H_2O$ and 0.14 mole of $Al(NO_3)_3 \cdot 9H_2O$ were used in place of 0.14 mole of $Cu(NO_3)_2 \cdot 3H_2O$ and 0.06 mole of $Al(NO_3)_3 \cdot 9H_2O$ and 0.40 mole of sodium carbonate was used in place of 0.345 mole of sodium carbonate. The composition of the resultant precursor was of an undeveloped hydrotalcite-like phase. An infrared spectroscopic analysis indicated the presence of aluminum hydroxide.

II. General Illustration with Reference to Drawings

FIG. 1 gives infrared absorption spectra, in which a) is for a precursor not containing aluminum hydroxide, b) is for a precursor in which an aluminum hydroxide phase has been formed, and c) is for a single aluminum hydroxide phase prepared for comparison by a precipitation method. Sharp peaks at 1387 $cm^{-1}$ and somewhat broad peaks at 1525 $cm^{-1}$ seen in b) and c) show the formation of an aluminum hydroxide phase.

FIG. 2 shows an X-ray diffraction for an undeveloped hydrotalcite-like phase; FIG. 3 gives an X-ray diffraction for a hydrotalcite-like phase developed by aging; and FIG. 4 denotes an X-ray diffraction for an undeveloped hydrotalcite-like phase with malachite mixed. Measurements of X-ray diffraction were made by means of a copper rotating anode of 50 kV and 200 mA using a monochrometer as the detecting element. In X-ray diffraction, where about 0.5% or more of a crystal phase is mixed, it is possible to determine it semi-quantitatively from the diffraction pattern. As is clear at a glance, it can be said that absolutely no malachite is present in FIGS. 2 and 3. Malachite is clearly present to a larger extent in FIG. 4 and hence the catalyst 9 is not satisfactory in view of activity.

III. Hydration Reaction of Nitrile

Examples 1 to 8

In a 100-ml glass reactor were charged 3 g of the catalyst 1, 2, 3, 4, 5, 6, 7 or 8 and 65 ml of an aqueous 15.4% acrylonitrile solution, and the contents were reacted at 70° C. for 2 hours while being stirred in a thermostat. The products were identified by liquid chromatography. The results are shown in Table 1.

Comparative Examples 1 to 5

Reaction was carried out in the same manner as in Example 1 except that the catalyst 9, 10, 11, 12 or 13 was used in place of the catalyst 1 in the method of Example 1. The results are given in Table 1.

TABLE 1

|  | Catalyst | $M^{3+}/M^{2+c)}$ | Conversion[a] | Selectivity[b] |
|---|---|---|---|---|
| Example |  |  |  |  |
| 1 | 1 | 30/70 | 72.4 | 99.3 |
| 2 | 2 | 20/80 | 68.4 | 99.6 |
| 3 | 3 | 45/55 | 68.1 | 99.1 |
| 4 | 4 | 30/70 | 72.6 | 99.2 |
| 5 | 5 | 30/70 | 70.8 | 99.7 |

TABLE 1-continued

|  | Catalyst | $M^{3+}/M^{2+c)}$ | Conversion[a] | Selectivity[b] |
|---|---|---|---|---|
| 6 | 6 | 25/75 | 70.3 | 99.2 |
| 7 | 7 | 30/70 | 72.0 | 99.4 |
| 8 | 8 | 30/70 | 70.1 | 99.2 |
| Comp. Ex. |  |  |  |  |
| 1 | 9 | 15/85 | 41.2 | 99.3 |
| 2 | 10 | 30/70 | 65.3 | 99.2 |
| 3 | 11 | 50/50 | 61.5 | 99.2 |
| 4 | 12 | 10/90 | 51.2 | 99.2 |
| 5 | 13 | 70/30 | 43.6 | 99.1 |

[a]Acrylonitrile conversion (%)
[b]Acrylamide selectivity (%)
[c]Atomic ratio of trivalent metal ions to divalent metal ions

We claim:

1. A method for preparing a copper catalyst for the hydration of a nitrile which comprises preparing a precursor with a hydrotalcite-like phase and containing no malachite and aluminium hydroxide by mixing an alkali with an aqueous solution containing copper ions and aluminum ions in which the atomic ratio of trivalent metal ions to divalent metal ions is in the range of from 20/80 to 45/55, in the absence of sodium hydroxide and potassium hyroxide, and reducing the precursor so as to form the catalyst.

2. A method for the hydration of a nitrile in which a copper catalyst used is prepared by preparing a precursor with a hydrotalcite-like phase and containing no malachite and aluminum hydroxide by mixing an alkali with an aqueous solution containing copper ions and aluminum ions in which the atomic ratio of trivalent metal ions to divalent metal ions is in the range of from 20/80 to 45/55, wherein said mixing is in the absence of sodium hydroxide and potassium hyroxide, and reducing the precursor so as to form the catalyst.

3. The method according to claim 1 wherein the atomic ratio of trivalent metal ions to divalent metal ions is in the range of from 25/75 to 30/70.

4. The method according to claim 1 wherein the alkali is the carbonate or hydrogencarbonate of at least one alkali metal selected from lithium, sodium, potassium, rubidium and cesium, ammonium carbonate or ammonium hydrogencarbonate.

5. The method according to claim 3 wherein the alkali is the carbonate or hydrogencarbonate of at least one alkali metal selected from lithium, sodium, potassium, rubidium and cesium, ammonium carbonate or ammonium hydrogencarbonate.

6. The method according to claim 1 wherein the precursor contains trivalent metal ions and divalent metal ions in an atomic ratio in the range of from 20/80 to 45/55.

7. The method according to claim 6 wherein the atomic ratio of trivalent metal ions and divalent metal ions of the precursor is in the range of from 25/75 to 30/70.

8. The method according to claim 1 wherein the hydrotalcite-like phase is obtained by forming a precipitate which is to be the precursor and then aging the precipitate at a temperature of from 60° C. to 200° C.

9. The method according to claim 3 wherein the hydrotalcite-like phase is obtained by forming a precipitate which is to be the precursor and then aging the precipitate at a temperature of from 60° C. to 200° C.

10. The method according to claim 4 wherein the hydrotalcite-like phase is obtained by forming a precipitate which is to be the precursor and then aging the precipitate at a temperature of from 60° C. to 200° C.

11. The method according to claim 5 wherein the hydrotalcite-like phase is obtained by forming a precipitate which is to be the precursor and then aging the precipitate at a temperature of from 60° C. to 200° C.

12. The method according to claim 8 wherein the temperature at which the precipitate is aged is from 80° C. to 120° C.

13. The method according to claim 9 wherein the temperature at which the precipitate is aged is from 80° C. to 120° C.

14. The method according to claim 10 wherein the temperature at which the precipitate is aged is from 80° C. to 120° C.

15. The method according to claim 11 wherein the temperature at which the precipitate is aged is from 80° C. to 120° C.

16. The method according to claim 2 wherein the atomic ratio of trivalent metal ions to divalent metal ions is in the range of from 25/75 to 30/70.

17. The method according to claim 2 wherein the alkali is the carbonate or hydrogencarbonate of at least one alkali metal selected from lithium, sodium, potassium, rubidium and cesium, ammonium carbonate or ammonium hydrogencarbonate.

18. The method according to claim 16 wherein the alkali is the carbonate or hydrogencarbonate of at least one alkali metal selected from lithium, sodium, potassium, rubidium and cesium, ammonium carbonate or ammonium hydrogencarbonate.

19. The method according to claim 2 wherein the precursor contains trivalent metal ions and divalent metal ions in an atomic ratio in the range of from 20/80 to 45/55.

20. The method according to claim 19 wherein the atomic raio of trivalent metal ions and divalent metal ions of the precursor is in the range of from 25/75 to 30/70.

21. The method according to claim 2 wherein the hydrotalcite-like phase is obtained by forming a precipitate which is to be the precursor and then aging the precipitate at a temperature of from 60° C. to 200° C.

22. The method according to claim 16 wherein the hydrotalcite-like phase is obtained by forming a precipitate which is to be the precursor and then aging the precipitate at a temperature of from 60° C. to 200° C.

23. The method according to claim 17 wherein the hydrotalcite-like phase is obtained by forming a precipitate which is to be the precursor and then aging the precipitate at a temperature of from 60° C. to 200° C.

24. The method according to claim 18 wherein the hydrotalcite-like phase is obtained by forming a precipitate which is to be the precursor and then aging the precipitate at a temperature of from 60° C. to 200° C.

* * * * *